US010431329B2

(12) United States Patent
Kagen

(10) Patent No.: US 10,431,329 B2
(45) Date of Patent: Oct. 1, 2019

(54) REAL-TIME SYMPTOM ANALYSIS SYSTEM AND METHOD

(71) Applicant: Steven L. Kagen, Appleton, WI (US)

(72) Inventor: Steven L. Kagen, Appleton, WI (US)

(*) Notice: Subject to any disclaimer, the term of this patent is extended or adjusted under 35 U.S.C. 154(b) by 926 days.

(21) Appl. No.: 14/633,631

(22) Filed: Feb. 27, 2015

(65) Prior Publication Data
US 2015/0242586 A1 Aug. 27, 2015

Related U.S. Application Data

(60) Provisional application No. 61/945,466, filed on Feb. 27, 2014.

(51) Int. Cl.
*G16H 10/20* (2018.01)
*G06F 19/00* (2018.01)
*G16H 50/30* (2018.01)

(52) U.S. Cl.
CPC ........... *G16H 10/20* (2018.01); *G06F 19/324* (2013.01); *G16H 50/30* (2018.01)

(58) Field of Classification Search
CPC ............ G06Q 50/24; G06Q 10/063; G06Q 10/06314; G06Q 10/02; G06Q 10/0635; A61B 5/00; A61B 5/01; A61B 5/02; A61B 5/7445; A61B 5/021; A61B 5/024; A61B 5/0816
See application file for complete search history.

(56) References Cited

U.S. PATENT DOCUMENTS

| | | | |
|---|---|---|---|
| 6,023,223 A | 2/2000 | Baxter, Jr. | |
| 7,676,384 B2 | 3/2010 | Baker et al. | |
| 8,123,683 B2 | 2/2012 | Stupp et al. | |
| 9,805,163 B1* | 10/2017 | Panch | G06F 19/325 |
| 2003/0036683 A1* | 2/2003 | Kehr | G06F 19/325 600/300 |
| 2006/0069915 A1* | 3/2006 | Koeda | G06F 21/126 713/168 |
| 2008/0091730 A1 | 4/2008 | Jung et al. | |
| 2008/0287746 A1 | 11/2008 | Reisman | |
| 2010/0312745 A1* | 12/2010 | Tabak | G06F 17/18 706/52 |
| 2010/0318424 A1 | 12/2010 | LaValle | |
| 2011/0184250 A1 | 7/2011 | Schmidt et al. | |
| 2012/0041778 A1* | 2/2012 | Kraft | G06F 19/00 705/2 |
| 2012/0084092 A1* | 4/2012 | Kozuch | G06Q 50/22 705/2 |
| 2012/0209082 A1 | 8/2012 | Al-Ali | |
| 2012/0253139 A1 | 10/2012 | Maman et al. | |
| 2013/0085345 A1 | 4/2013 | Geisner et al. | |
| 2014/0114680 A1 | 4/2014 | Mills et al. | |
| 2014/0236622 A1 | 8/2014 | Southam | |

(Continued)

*Primary Examiner* — Reginald R Reyes
(74) *Attorney, Agent, or Firm* — Butzel Long, PC; Gunther J. Evanina

(57) ABSTRACT

A system and method for presenting real-time health information administers virtual questionnaires, automatically determines a user health status, and presents a visualization to a user indicating a likelihood of a symptom occurrence. The system and method presents results of the analysis to a user to predict health risks, analyze user symptoms, connect users with medical professionals, and provide marketing offers. The results may be presented as text, graphs, stationary maps, and/or animated maps.

20 Claims, 9 Drawing Sheets

(56) References Cited

U.S. PATENT DOCUMENTS

2014/0244296 A1\* 8/2014 Linn ................... G16H 40/20
  705/3
2014/0372133 A1\* 12/2014 Austrum ............ G06F 19/3475
  705/2

\* cited by examiner

REAL-TIME SYMPTOM ANALYSIS SYSTEM AND METHOD

CROSS-REFERENCE TO RELATED APPLICATION

This application claims the benefit of provisional patent application Ser. No. 61/945,466, filed Feb. 27, 2014.

BACKGROUND OF THE INVENTION

1. Field of the Invention

The present disclosure relates to a system and method for providing health analysis. Specifically, the present disclosure relates to a symptom analysis application and method for creating, analyzing, individualizing, geo-locating, and displaying information regarding symptoms of allergy, asthma, sinus headaches, migraine, arthritis, and other medical conditions induced by a person's unique responses to environmental exposures to allergens, air pollutants, and weather elements instantaneously in real time.

2. Description of Related Art

A large proportion of the population suffers from allergy symptoms. Allergic reactions are typically caused by the interaction of a person's immune system with external and environmental factors. For example, foreign proteins such as those found in pollens, molds, and dust mites may cause an immune reaction in any person having a particular genetic sensitivity. If the immune reaction induced by these foreign proteins involves certain antibodies, the possibility of an allergic reaction exists.

However, each patient with allergy or asthma issues is unique and will respond differently to different aggravating factors. For example, one person may be very sensitive to air pollutants but have little reaction to mold spores, whereas another person may have no reaction to air pollutants but a severe reaction to pollens.

Allergic reactions may range from mild annoyances to severe and potentially life-threatening events. For example, asthma is caused by allergic reactions within the airways of the lungs. If left untreated and uncontrolled, asthma may be life threatening or result in a form of permanent emphysema. In order to prevent such long-term effects, it is desirable to predict when and where allergy and/or asthma events may occur.

However, an accurate prediction requires accurate information as to a person's activities and health. Simply asking the person about their activities and health introduces a high degree of subjectivity into the prediction, and therefore reduces the accuracy of the prediction. Moreover, asking the person to provide information regarding past events may introduce hindsight bias or other memory errors, and thus further reduce the accuracy of the prediction.

To that end, there exists a need for a system and method to obtain both subjective and objective information, in real-time, regarding a person's health. Moreover, there exists a need for a system and method to correlate this information with environmental data for the person's particular location, also in real-time. The proliferation of mobile devices (such as smartphones) provides a possible path to such a solution, but is fraught with difficulties. For example, inefficiencies arising out of existing tools may result in increased bandwidth and/or computational footprint. Moreover, existing tools may be unduly invasive, leading potential users to reject them. These challenges, particular to the Internet and the field of mobile-device-assisted health monitoring, make it difficult to provide an effective solution. To overcome such a problem specifically arising in the realm of computer networks, a solution necessarily rooted in computer technology must be developed.

BRIEF SUMMARY OF THE INVENTION

A system and method provides an application, such as a software application, for aggregating and analyzing data from multiple sources to support a presentation of information regarding an individual's symptoms of allergy, asthma, sinus headaches, migraine, arthritis, and other medical conditions by accumulating data; performing various calculations to the accumulated data; and outputting a data visualization for the symptom analysis based upon the results of the calculations.

In an aspect of the present disclosure, a method of presenting real-time health information is described, the method comprising: administering by a user interface associated with a mobile device a virtual questionnaire; automatically by a processor associated with the mobile device determining an instantaneous user health status; and presenting by a display associated with the mobile device a visualization indicative of a likelihood of a symptom occurrence, wherein determining the instantaneous user health status includes at least one of determining a location stamp from a location determination circuit associated with the mobile device, determining a timestamp from a clock associated with the mobile device, determining a severity score from a user input at the user interface, and storing the instantaneous user health status in a data store associated with the mobile device.

In another aspect of the present disclosure, a system for presenting real-time health information is described, the system comprising: a data store; and a mobile device coupled to the data store and programmed to: administer by a user interface associated with a mobile device a virtual questionnaire; automatically by a processor associated with the mobile device determine an instantaneous user health status; and present by a display associated with the mobile device a visualization indicative of a likelihood of a symptom occurrence, wherein determining the instantaneous user health status includes at least one of determining a location stamp from a location determination circuit associated with the mobile device, determining a timestamp from a clock associated with the mobile device, determining a severity score from a user input at the user interface, and storing the instantaneous user health status in the data store.

In so doing, various aspects of the present disclosure provide for improvements in the underlying technological field of real-time health monitoring via a mobile device, as well as related technological fields. Moreover, various aspects of the present disclosure provide for increased efficiencies in the use of computer resources such as processor time and memory, as well as Internet resources such as bandwidth and server overhead.

The present disclosure can be embodied in various forms, including business processes, application-specific computer implemented methods, computer program products, computer systems and networks, user interfaces, application programming interfaces, and the like. The foregoing summary is intended merely to provide a general overview of various aspects of the present disclosure, and is not intended to limit the scope of this application in any way.

DESCRIPTION OF THE DRAWINGS

These and other more detailed and specific features of the above aspects are more fully disclosed in the following specification, reference being had to the accompanying drawings, in which.

DETAILED DESCRIPTION

A system and method provides for aggregating and analyzing data from multiple sources to support a presentation of information regarding symptoms and environmental factors (i.e. allergens, weather elements, pollution, etc.) through an interface.

For example, the system and method may aggregate symptom data (for example, user data and/or environmental data) into a data structure obtained from a user and from multiple databases and/or environmental sensors and, upon user input, appropriately weight and combine the data to generate sub-scores and a risk score that reflects the users unique risks of experiencing symptoms of a given medical condition. The system and method may further transform the data and scores into a visualization for presentation to the user.

User data may include real-time user data and historical user data. Real-time user data may be recorded on a form, an example of which may be an application-generated questionnaire, that provides multiple sections with multiple data fields, each field containing data that may contribute to a symptom score. Historical data may include a database of previously-collected real-time user data. Examples of user data fields include, but are not limited to, data regarding allergy and asthma symptoms as will be described in more detail below.

Environmental data may include real-time environmental data and historical environmental data corresponding to characteristics of the user's local environment. Examples of characteristics and characteristic types include, but are not limited to temperature, humidity, wind speed and direction, pollen levels, mold spore levels, virus prevalence, wind, precipitation, ozone levels, particulate matter levels, and other environmental factors as will be discussed in more detail below. Environmental data may be stored in a public or private database, including databases operated by the United States National Weather Service (NWS), Environmental Protection Agency (EPA), National Oceanic and Atmospheric Administration (NOAA), and others, and may be public domain and/or proprietary.

Thus, in an operational example, the system and method may be utilized to aggregate into a data structure user and environmental data, accumulate values on a characteristic basis for specific health conditions from the data structure, curate the values to output scores and visual data for presentation through an interface. In this manner, the interface may present a comprehensive and comprehensible assessment of a user's unique risk for experiencing various health conditions that would not otherwise be available.

Figure 1:
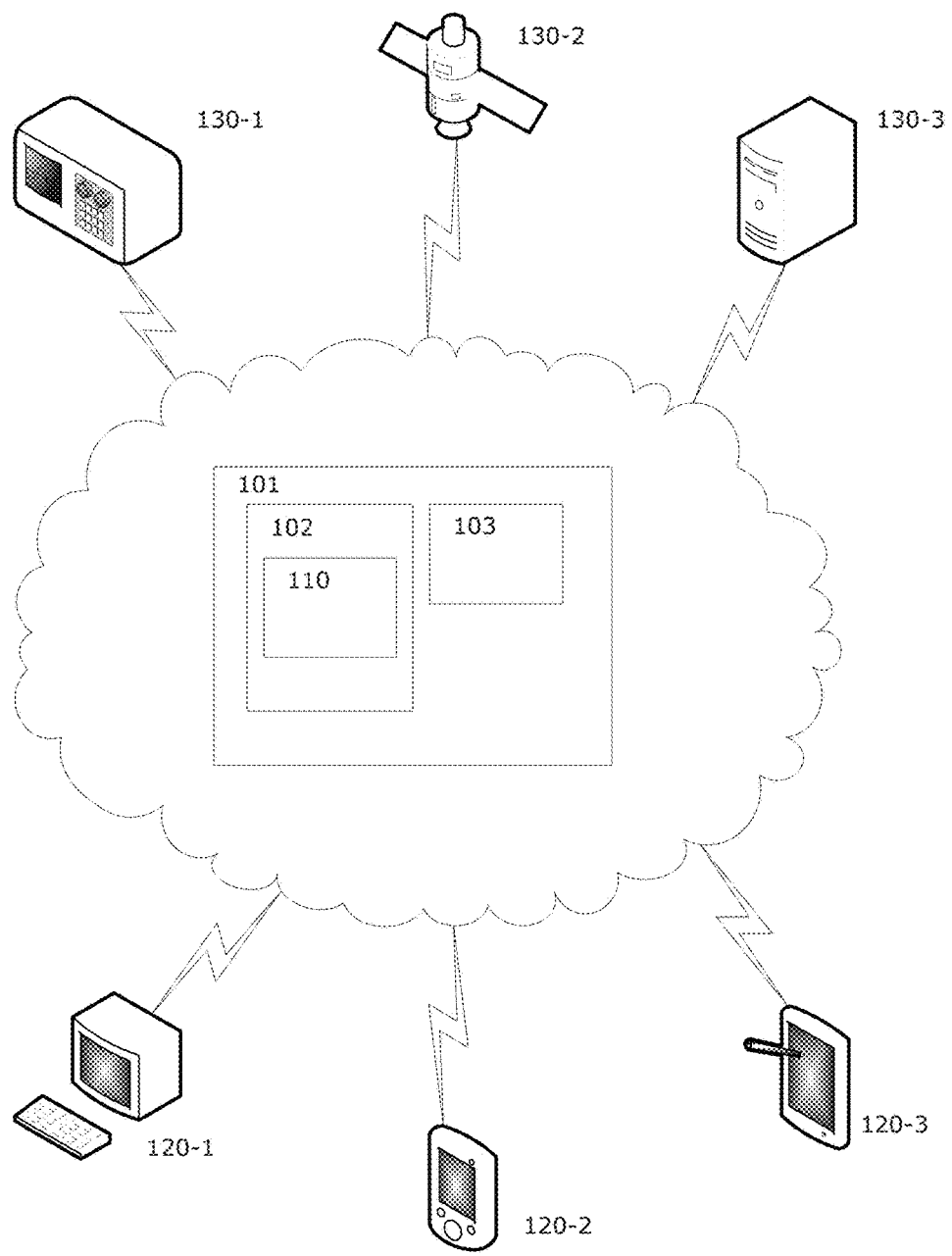
FIG. 1 illustrates an exemplary system in which a symptom analysis application operates.

FIG. 1 illustrates an exemplary system 100 that includes a symptom analysis device 101 having a central processing unit (CPU or "processor") 103 and a memory 102 on which a symptom analysis application 110 (hereinafter referred to as application 110) is stored. System 100 further includes at least one user device 120-1, 120-2, . . . , 120-n (collectively referred to as user devices 120) and at least one data source 130-1, 130-2, . . . , 130-m (collectively referred to as data sources 130). Although not expressly illustrated, user devices 120 and data sources 130 similarly include respective processors and memories.

For example, in response to receiving an input from a user device 120, the symptom analysis device 101 may utilize application 110 stored on memory 102 to aggregate data relating to allergy symptoms and aeroallergens from one or more of the data sources 130 and/or user devices 120 (e.g., via a communication link). The particular operation of application 110 will be described in more detail below.

The exemplary user device 120 and/or data source 130 may be any computing system and/or device that includes a processor and a memory. In general, computing systems and/or devices may employ any of a number of computer operating systems, including, but by no means limited to, versions and/or varieties of the Microsoft Windows® operating system; the Unix operating system (e.g., the Solaris® operating system distributed by Oracle Corporation of Redwood Shores, Calif.); the AIX UNIX operating system distributed by International Business Machines of Armonk, N.Y.; the Linux operating system; the Mac OS X and iOS operating systems distributed by Apple Inc. of Cupertino, Calif.; the BlackBerry OS distributed by Research In Motion of Waterloo, Canada; and the Android operating system developed by the Open Handset Alliance. Examples of computing devices include, without limitation, a computer workstation, a server, a desktop, notebook, laptop, or handheld computer, a cellular phone, a smartphone, a personal digital assistant (PDA), a tablet computer, a remote sensor network, a weather radar device, or any other computing system and/or device. Here, the exemplary user device 120 includes a location determination circuit such as a satellite-based location circuit (e.g. GPS) or a cellular-based location circuit (e.g. via triangulation); a clock; a display; a user input device such as a touchscreen or a keyboard; and a data store such as a memory chip or memory card.

Computing systems and/or devices generally include computer-executable instructions (e.g., application 110), where the instruction may be executable by one or more computing devices such as those listed above. Computer-executable instructions may be compiled or interpreted from computer programs created using a variety of programming languages and/or technologies, including, without limitation, and either alone or in combination, Java™, C, C++, Visual Basic, Java Script, Perl, etc.

A processor, such as processor 103, may include processes comprised from any hardware, software, or combination of hardware or software that carries out instructions of a computer program by performing logical and arithmetical calculations, such as adding or subtracting two or more numbers, comparing numbers, or jumping to a different part of the instructions. For example, the processor 103 may be any one of, but not limited to single, dual, triple, or quad core processors (on one single chip), graphics processing units, visual processing units, and virtual processors.

The exemplary system 100 and exemplary computing devices may take many different forms and include multiple and/or alternate components and facilities, e.g., as illustrated in the description provided below. While exemplary systems are shown and described, the exemplary components illustrated in the figures are not intended to be limiting; indeed, additional or alternative components and/or implementations may be used.

Furthermore, the processor of computing systems and/or devices may receive instructions from the memory (e.g., memory 102) and execute these instructions, thereby performing one or more processes, including one or more of the processes described herein (e.g., the operations of aggregating, accumulating, evaluating, weighting, curating, transforming, and/or presenting information). Such instructions and other data may be stored and transmitted using a variety of computer-readable media, such as memory 102.

Memory 102 may be, in general, any computer-readable medium (also referred to as a processor-readable medium) that may include any non-transitory (e.g., tangible) medium that participates in providing data (e.g., instructions) that may be read by a computer (e.g., by processor 102 of devices 101, 120, and/or 130). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including radio waves, metal wire, fiber optics, and the like, including the wires that comprise a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

In some examples, the elements of devices 101, 120, 130 may be implemented as computer-readable instructions (e.g., software) on one or more computing devices (e.g., servers, personal computers, etc.), stored on computer readable media associated therewith (e.g., disks, memories, etc.). A computer program product may comprise such instructions stored on computer readable media for carrying out the operations described herein.

Devices 101, 120, 130 may generally be any electronic hardware that includes a memory 102 and processor 103 and is capable of receiving and processing inputs (e.g., user entered data that provides indication of a selection of a field or instance of a user interface as described below) and sending/receiving electronic data transfers (e.g., via wired or wireless communication links) to and from the systems that include those inputs.

Devices 101, 120, 130 may further include a display, support interfaces, and/or communicate within the exemplary scheme 100. A display is an output device for presentation of information in visual or tactile form, such as interfaces or web portals. Examples of display may include, without limitation, cathode ray tube display, light-emitting diode display, electroluminescent display, electronic paper, plasma display panel, liquid crystal display, high-performance addressing display, thin-film transistor display, organic light-emitting diode display, surface-conduction electron-emitter display, laser TV, carbon nanotubes, quantum dot display, interferometric modulator display, and the like. Thus, a display of any device 101, 120, 130 may generate and/or present interfaces or a web portal to a user, such that the user may interact with and receive information from other computing devices 120, 130 or the symptom analysis device 101.

In general, a network (e.g., system 100) may be a collection of computers and/or other hardware to provide infrastructure to establish virtual or physical connections and carry communications. For instance, a network may be an infrastructure that generally includes edge, distribution, and core devices and enables a path for the exchange of information between different devices and systems. Furthermore, a network may utilize any conventional networking technology and may, in general, be a packet network (e.g., any of a cellular network, global area network, wireless local area network, wide area network, local area network, or combinations thereof) that provides the protocol infrastructure to carry communications. System 100 is merely representative, and thus while a single cloud illustrates central symptom analysis device 100, these illustrations may represent a single network, a combination of different network components and technologies, and/or a plurality of networks as described above.

Individual communication links may utilize any antenna technology, such as cellular, Wi-Fi, near field communication (NFC), Bluetooth®, or the like, which is used to exchange data wirelessly using electromagnetic waves. Alternatively or in combination therewith, individual communication links may utilize wired connections, such as metal wires, fiber optics, and the like. As such, devices 101, 120, 130 may further include, without limitation, networking hardware such as gateways, routers, network bridges, switches, hubs, repeaters, multilayer switches, protocol converters, proxy servers, firewalls, network address translators, multiplexers/demultiplexers, network interface controllers, modems, ISDN terminal adaptors, line drivers, networking cables, input/output ports, and the like.

While exemplary system 100 as particularly illustrated shows the symptom analysis application 110 as residing on a centralized symptom analysis device 101, this disclosure is not so limited. In particular, application 110 may reside wholly or in part on one or a combination of user devices 120, for example as a downloadable application. As such, application 110 may be run wholly by a processor contained in a user device 120, or may be run in a distributed fashion (for example, by cloud computation) across several user devices 120 and/or centralized symptom analysis device 101.

Figure 2:
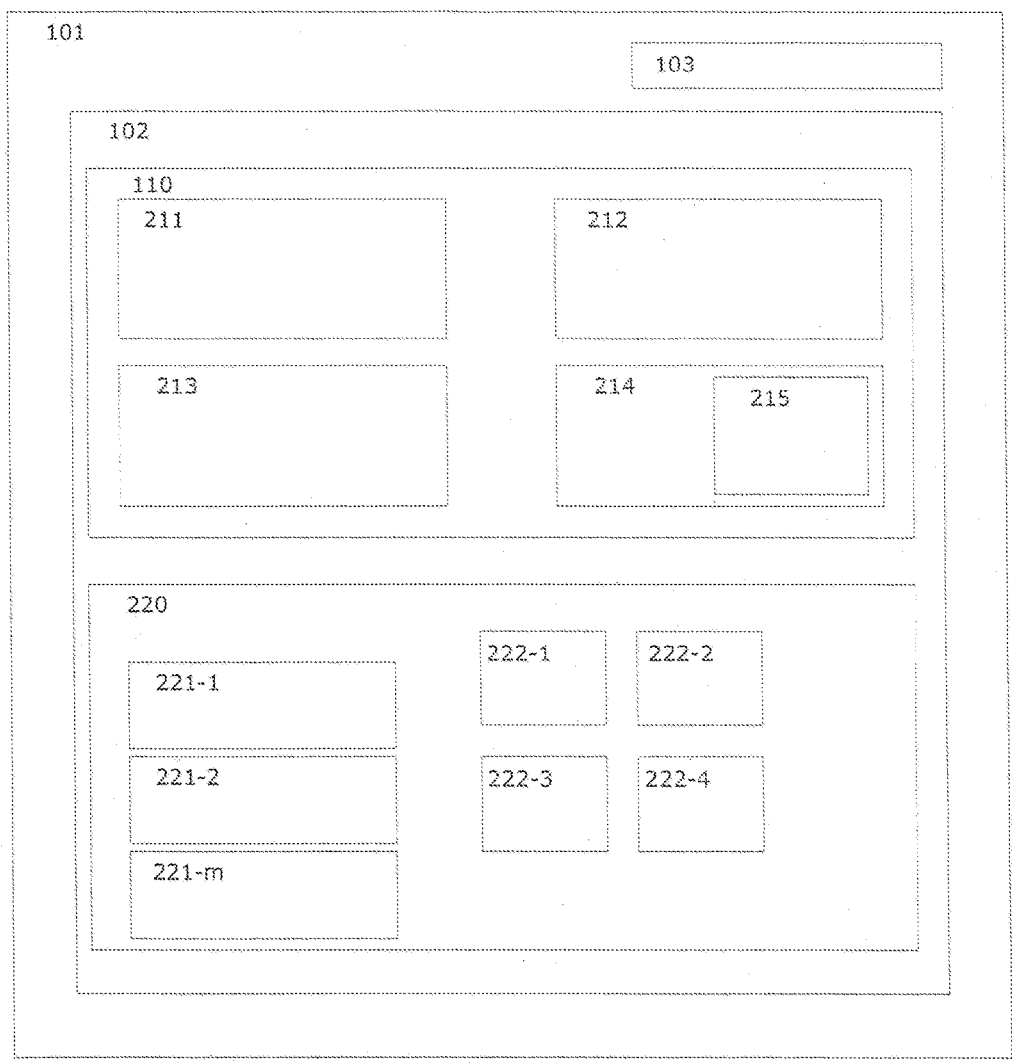
FIG. 2 illustrates an exemplary modular schematic of a symptom analysis application.

FIG. 2 illustrates an exemplary symptom analysis application 110 and database 220 stored on a memory 102 of any of the devices 101, 120, 130 as described above.

Application 110 is configured to process allergen information. Application 110 includes a data accumulation module 211, a calculation module 212, a presentation module 213, and an interface module 214, which is configured to generate a user interface 215. Although one particular modular breakdown of application 110 (and database 220) is illustrated, one of ordinary skill in the art will recognize that the same functionality may be provided using fewer, greater, or differently named modules. For example, any two or more of the above modules may be integrated with one another into a single module.

Individual modules 211-215 may manage the dispatch and receipt of data/information along with other applications and/or drivers, as necessary per operating system. A driver may be a computer routine that controls a particular physical component of a device or a peripheral (e.g., a printer, display, input device, or the like) attached to the device.

Thus, an individual module may manage and translate input/output requests into data processing instructions for the central processing unit (e.g., processor 103) and may include a set of executable instructions that itemizes and implements the data structure, object classes, and variables that interact with the drivers to operate physical components and that launch routines and/or programs (e.g., send and receive instructions, data, and/or information to and from individual modules, applications, and/or devices).

Data accumulation module 211 includes a set of executable instructions configured to perform accessing and accumulating operations. Data accumulation module 211 is preferably configured to access a plurality of databases (e.g. database 220) and records contained therein and prepare information contained therein for future access as will be described in more detail below.

Calculation module 212 includes a set of executable instructions configured to perform weighting and calculating functions. Calculation module 212 is preferably configured to receive data from data accumulation module 211 and perform appropriate calculations as will be described in more detail below.

Presentation module 213 includes a set of executable instructions configured to perform presentation, display, and notification functions. Presentation module 213 is preferably configured to receive calculations from calculation module 212, apply a rule set to the calculations, and selectively output results to a user as will be described in more detail below.

The interface module 214 may be an application programmable interface that includes a set of executable instructions for generating and managing user interfaces 215, which receive inputs and present information. For instance, the interface module 214 may be configured to generate, present, and provide one or more user interfaces 215 in a menu, icon, tabular, map, pop-up, grid format etc. (e.g., as illustrated in FIGS. 3-4) in connection with other modules for presenting information and receiving inputs (e.g., indications of altering, updating, or changing the codes, profiles characteristics, and/or user preferences on records). The inputs received by the user interfaces 215 may generally be communicated by interface module 214 to the other modules, which may in turn forward the inputs to the still other modules for processing.

User interfaces 215 may include any presentation of information or data, such as suggested information or search results, through a display (as described above), whether graphically or otherwise, where interaction between a user and application 110 is necessary or desired. Examples of user interfaces 215 may include a data manipulation interface, a graphical user interface (GUI), a touchscreen interface, a text-based interface, etc. User interfaces 215 may receive inputs indicating user selections and/or user instructions, e.g., inputs indicating codes for translation into plain language by user interfaces 215. User interfaces 215 may also include any presentation of information or data through frame, fields, banners, icons, badges, alerts, sounds, text, or any combinations thereof. A frame may be a reserved space of an interface that presents alphanumeric text and/or graphical items presenting records and may also be a mechanism for receiving input that causes the application 110 to perform additional operations. A field may be a reserved space of an interface that presents alphanumeric text and/or menu items records and may also be a mechanism for receiving input that causes the application 110 to perform additional operations. A banner may be a media or dropdown menu that extends from a top portion of an interface, a sub-interface, and/or display and that may include text, badges, and animated symbols. An icon and/or a badge may be a number or symbol that signals a link, an event, or a number of events. An alert may be a pop-up window that may be oriented within the display (e.g., centered) and that may include text, badges, and animated symbols.

Thus, the interface module 214 may generate new and unique user interfaces 215 particular to the application 110. That is, the interface module 214 may also commandeer or utilize interface formatting local to the device in which application 110 is stored. The interface module 214 may also provide remote interface formatting for a device in which only a portion of application 110 is stored (e.g., providing web portal interfaces for user devices 120 through which the symptom analysis device 101 may provide information and receive inputs). The interface module 214 may thus generate or utilize local, terminal, web-based, and mobile interfaces and any similar interface which presents and receives information relative to the devices 101, 120, 130.

Database 220 may be a data repository or other data store that includes any type of data structure, source, and/or file system that manages and stores records, such as records 221-1, 221-2, . . . , 221-*m* (collectively referred to as records 221), which in turn may comprise subrecords 222-1, 222-2, . . . , 222-*n* (collectively referred to as subrecords 222) described below. Database 220 may further include various kinds of mechanisms, including a hierarchical database, a set of files in a file system, an application database in a proprietary or open format, a relational database management system (RDBMS), etc., for storing, providing, accessing, and retrieving various kinds of data. Data may include the records and the information contained therein. The records may further be identified by metadata or an identifier, such as a file name, identification number, and/or other information unique to the record.

Each individual record 221 may correspond to user data for a particular symptom (i.e., an allergy), or to environmental data for a particular characteristic of the environment. Records 221 may respectively comprise a plurality of subrecords 222. A particular subrecord 222 may correspond to a historical data point for the particular record 221 to which subrecord 222 belongs. For example, record 221-1 may correspond to user data for environmental pollen count. In this example, each subrecord 222 belonging to record 221-1 may correspond to a previous measurement value of the environmental pollen count. That is, subrecord 222-1 in this example may be a measurement value of a specific local environmental pollen level one day ago; subrecord 222-2 may be a measurement value of the environmental pollen level two days ago, and so forth.

Each such data store may also generally be included within or external to a computing system and/or device (e.g., devices 101, 120, 130) employing a computer operating system such as one of those mentioned above, and/or accessed via a wired or wireless network or connection in anyone or more of a variety of manners. A file system may be accessible from a computer operating system, and may include files stored in various formats. A database (such as an RDBMS) generally employs the Structure Query Language (SQL) in addition to a language for creating, storing, editing, and executing stored procedures, such as the PL/SQL language mentioned above. Thus, devices 101, 120, 130 may include, for example, at least one of a weather database, public record database, user history database, medical professional database, etc.

Furthermore, although FIG. 2 illustrates an example wherein modules 211-215 are present within a single device, individual modules may be distributed across multiple devices. For example, data accumulation module 211 and calculation module 212 may be present on a centralized symptom analysis device 101, while presentation module 213 and interface module 214 may be present on a user device 120. Similarly, although FIG. 2 illustrates database 220 being present within the same device as application 110, database 220 may be separately configured. For example, database 220 may be present on a centralized symptom analysis device 101 and/or a data source 130, while application 110 may be present on a user device 120. By extension, portions of database 220 and individual modules of application 110 may be commonly or separately distributed across several different devices 101, 120, 130; for example, to allow for cloud computation or increased data security.

Figure 3A:
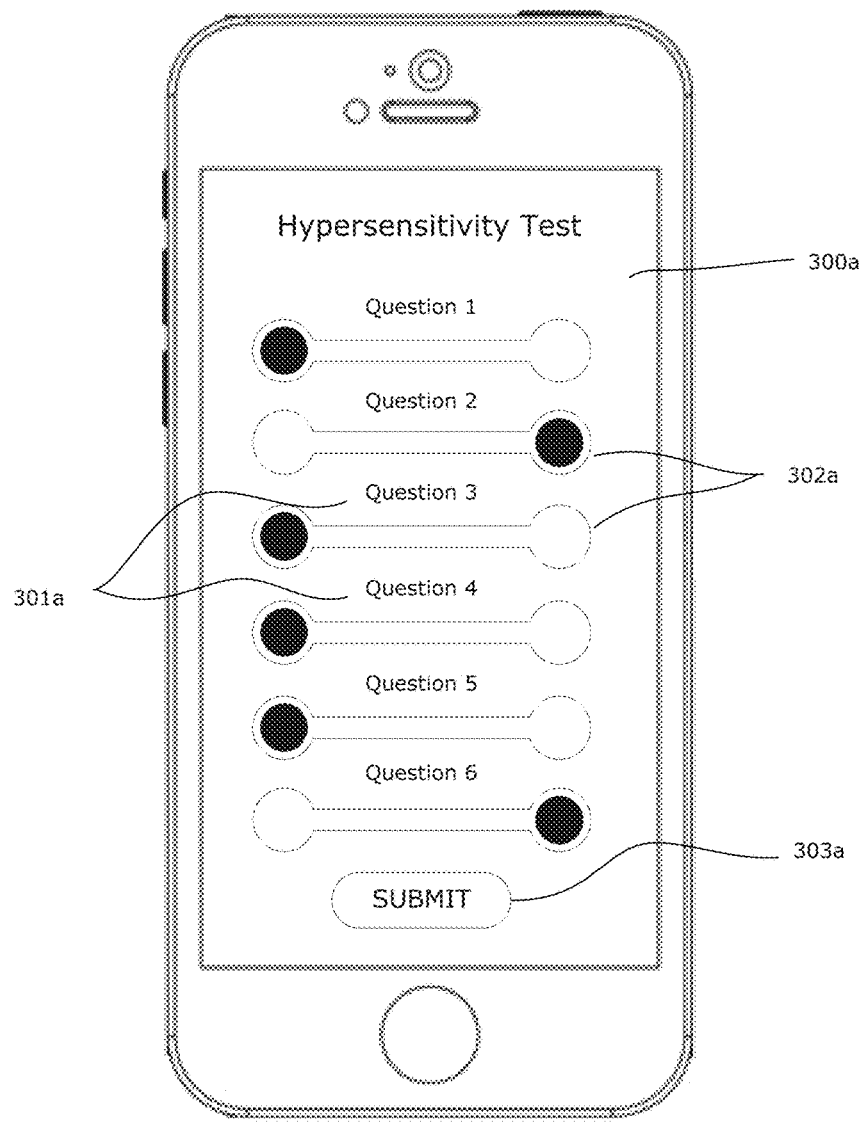
FIG. 3A illustrates an exemplary sensitivity questionnaire interface generated by a symptom analysis application.
Figure 4:
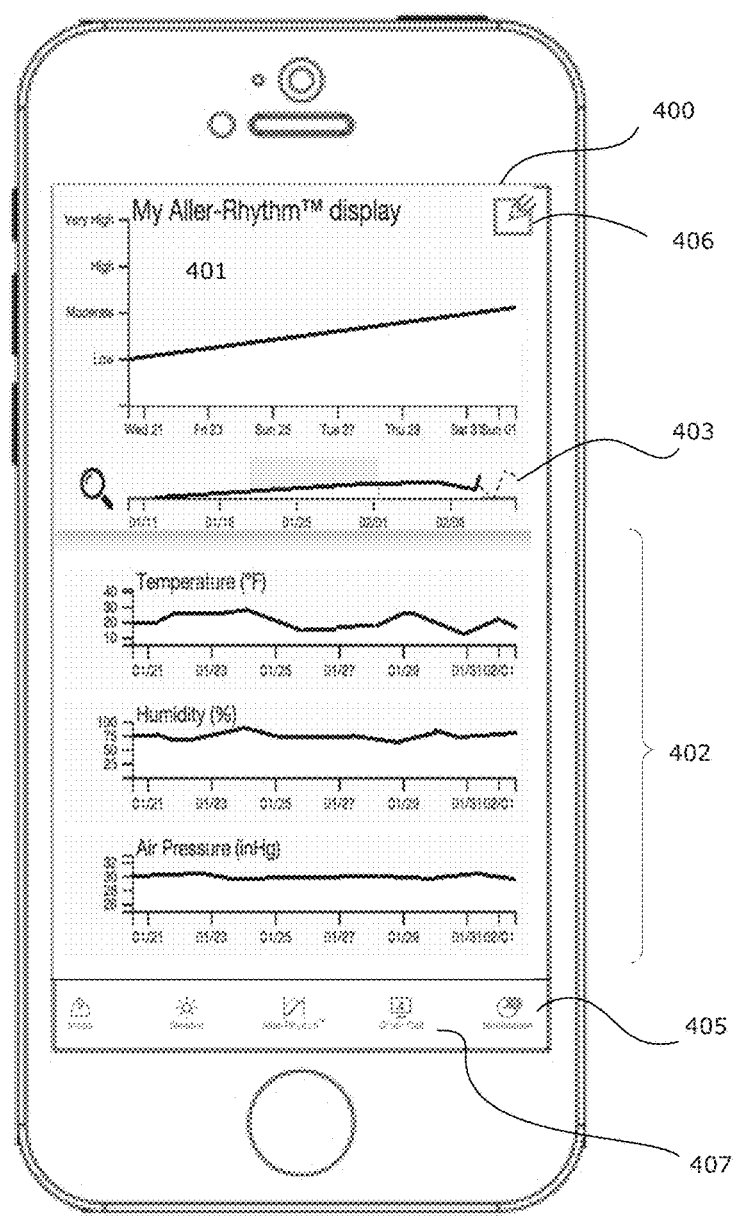
FIG. 4 illustrates another exemplary interface generated by a symptom analysis application.

FIG. 3A illustrates an exemplary questionnaire interface 300a (i.e., a "virtual questionnaire") generated by application 110. Interface 300a is a query interface configured to determine introductory characteristics of the user, such as the user's sensitivity to environmental stimuli.

Application 110 is preferably configured to administer a questionnaire via interface 300a to a user as an initial matter; for example, the first time a user runs application 110. Alternatively, application 110 may be configured to administer the questionnaire again at a later date; for example yearly or seasonally. Moreover, application 110 may be configured to administer the questionnaire again upon user request; for example, if the user has recently experienced a major life event such as severe illness, pregnancy, moving to a different region, and the like. The questionnaire may be a global questionnaire configured to query the user's health across a plurality of symptoms.

Interface 300a administers a plurality of queries 301a. In the exemplary illustration of FIG. 3A, interface 300a administers queries regarding sensitivity to a plurality of different stimuli. The user responds to queries 301a by selecting from a plurality of responses on an input form 302a. Where a particular query 301a requires a single response, input form 302a may be, for example, a radio button, a pull-down menu, a text box, or the like. Where a particular query 301a permits multiple responses, input form 302a may be, for example, a checklist or the like. Here, input form 302a is shown as a pair of connected radio buttons for each query 301a; for example, corresponding to a question with a Yes/No answer. In this manner, the user may select (for example, via a "tap" operation) the bubble corresponding to the appropriate answer to query 301a. Preferable queries 301a query a user's sensitivity to sunlight, perfume, exhaust, smoke, cold air, and the like. Additionally, queries 301a may query whether a user experiences certain conditions, such as cold or clammy extremities, mid-day sleepiness, migraines, ticklishness, indigestion, changes during ovulation, and the like. Moreover, queries 301a may query whether a user performs particular acts, such as taking very hot showers.

Once a user has completed the questionnaire, the user may submit the completed questionnaire by selecting a submit button 303a. Once submit button 303a has been selected, application 110 may store the responses, send the responses to a database of the type described above, perform calculations or manipulations on the responses, present the responses to the user, or the like. For example, application 110 may analyze the responses to calculate an overall hypersensitivity score for the user. This score allows application 110 to more accurately predict the user's responses to weather, pollutants, irritants, pollens, mold spores, and internal chemical changes within their body. Additionally, application 110 may further determine whether there are additional questionnaires to be completed, and may present these additional questionnaires to the user for completion in a similar fashion.

Figure 3B:
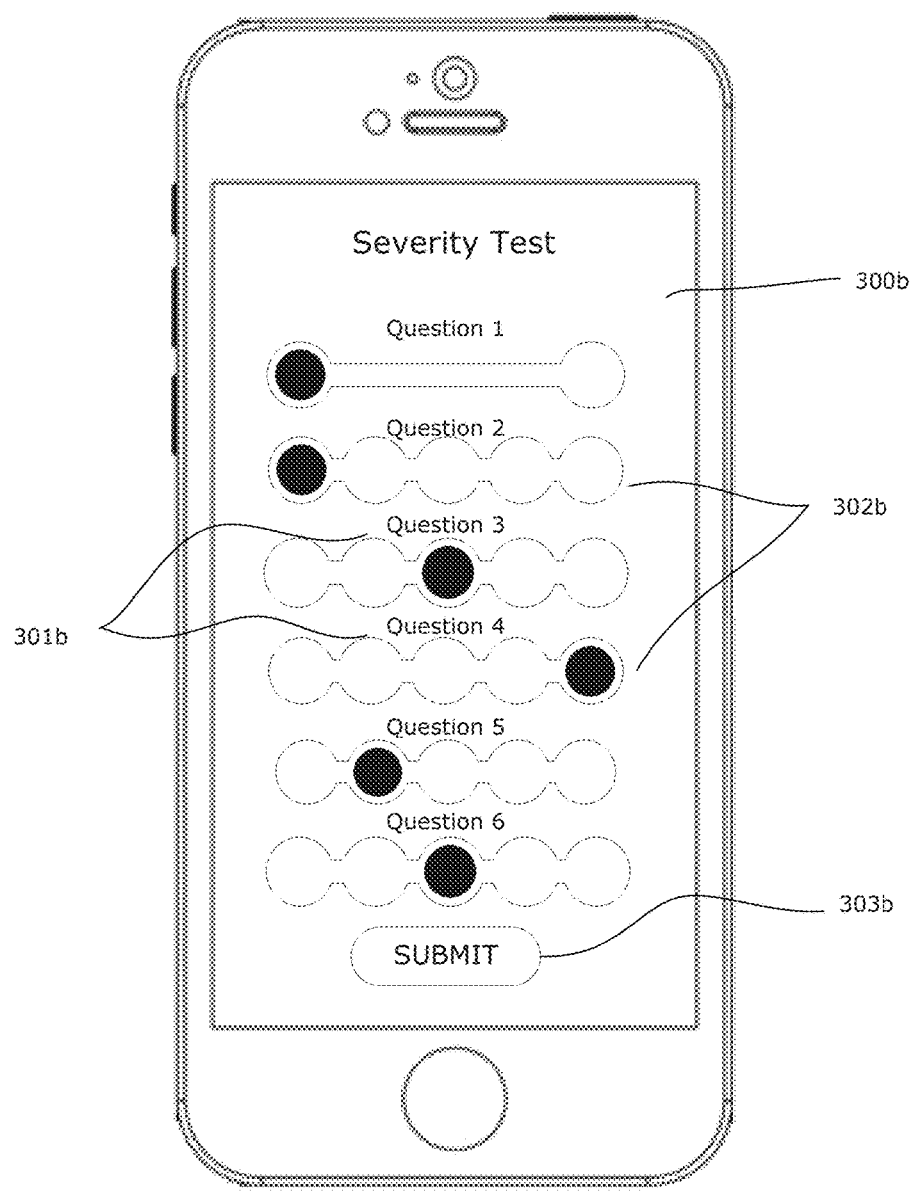
FIG. 3B illustrates an exemplary symptom questionnaire interface generated by a symptom analysis application.

FIG. 3B illustrates another exemplary questionnaire interface 300b (i.e., a "virtual questionnaire") generated by application 110. Interface 300b is a query interface configured to query a user regarding the user's subjective disease-specific symptoms.

Application 110 is preferably configured to administer a questionnaire via interface 300b to a user at a predetermined interval; for example, daily or weekly. Alternatively, application 110 may be configured to administer the questionnaire upon user input. The questionnaire may be unique to specific disease-related symptoms, or may be a global questionnaire configured to query the user's health across a plurality of symptoms.

Interface 300b administers a plurality of queries 301b. In the exemplary illustration of FIG. 3B, interface 300b administers queries regarding medication, nasal congestion, runny nose, itching, sneezing, mucus, and the like to determine the severity of the user's allergies. The user responds to queries 301b by selecting from a plurality of responses on an input form 302b. Where a particular query 301b requires a single response, input form 302b may be, for example, a radio button, a pull-down menu, a text box, or the like. Where a particular query 301b permits multiple responses, input form 302b may be, for example, a checklist or the like. Here, input form 302b is shown as a number of connected radio buttons for each query 301b. In this manner, the user may select (for example, via a "tap" operation) the bubble corresponding to the appropriate answer to query 301b. For example, if a particular query is "Did you sneeze today?" a user may select from bubbles corresponding to "Never", "Rarely", "At times", "Often", or "Extremely Often" as appropriate.

Once a user has completed the questionnaire, the user may submit the completed questionnaire by selecting a submit button 303b. Once submit button 303b has been selected, application 110 may store the responses, send the responses to a database of the type described above, perform calculations or manipulations on the responses, present the responses to the user, or the like. Additionally, application 110 may further determine whether there are additional questionnaires to be completed, and may present these additional questionnaires to the user for completion in a similar fashion.

FIG. 4 illustrates an exemplary visualization interface 400 generated by application 110. Interface 400 is a graphical display configured to apprise the user of historical data regarding environmental and/or user factors.

Application 110 is preferably configured to present data via interface 400 upon request by a user. Alternatively, application 110 may present interface 400 upon application start-up, upon completion of a questionnaire of the type described above, as a desktop widget for continuous viewing, or the like.

Interface 400 may present data in a graphical format, for example via graph 401. Graph 401 presents historical data for a particular environmental or user data type individually or for a plurality of environmental and user data types simultaneously. For example, graph 401 may present a previous week's historical temperature, wind speed, and pressure, which may be overlaid with a graph representing the user's historical responses to questionnaires of the type described above.

Graph 401 is preferably created by algorithmically comparing symptom scores generated by responses to queries (such as those presented by interface 300 above) with changes in the user's local environmental factors. Specifically, graph 401 preferably corresponds to a comparison between user responses and one or more of precipitation, temperature, humidity, air pressure, ozone level, particulate matter level, water vapor, uplift data, helicity, etc. In this manner, the visual display becomes more accurate over time when the user regularly completes questionnaires as the user's unique and individualized symptom score history becomes statistically more accurate.

Interface 400 may further include a plurality of visualization options identified in sub-interface 402. For example, interface 400 may present the user with a list of symptoms, allergens, data types, or the like, and the user may select the particular elements to be displayed via graph 401. In the particular example illustrated in FIG. 4, sub-interface 402 presents the user with a list of environmental factors to display: pollen from all grasses, Bermuda grasses, temperature, humidity, pressure, etc. Individual options contained in sub-interface 402 may be presented in one list or, as illustrated, may be grouped into categories. In this manner, the user may expand a list by selecting the appropriate category.

Additionally, interface 400 may present the user with a plurality of graph options presented in sub-interface 403; for example, regarding the length of historical data to display, the type of graph 401 to display, metric or English unit preference, notification options, and the like. In the particular example illustrated in FIG. 4, sub-interface 403 presents the user with a series of time periods whereby the user can control the length of historical data to display. Additionally, sub-interface 404 identifies specific environmental factors that have changed in association with a simultaneous change in the user's symptom scores on that day. Here, sub-interface 403 additionally displays predicted future data for the user's symptom forecast, shown as a dotted line corresponding to future dates (for example, 4-7 future days). This predicted symptom forecast may be based upon a statistical comparison of the user's past severity test scores along with predicted weather, pollution, and allergen factors.

Additionally, because graph 401 is based at least in part upon symptoms scores that are unique to a particular user, graph 401 (i.e., the "Aller-Rhythm™" display) provides a comparison between objective environmental factors and subjective user factors that is uniquely tailored to the particular user. Therefore, graph 401 together with sub-interface 404 provides information to the user revealing the probable cause (or causes) of the user's symptoms for a specific medical condition (or conditions).

As illustrated in FIG. 4, graph 401 presents the user with historical data regarding symptom severity (e.g., the "Aller-Rhythm™" display). Here, graph 401 corresponds to a particular date range as selected by the user using sub-interface 403. As such, graph 401 corresponds to a zoomed-in or blown-up sub-range of the graph displayed in sub-interface 403. Thus, a user may select a range by tapping or sliding on sub-interface 403, and the selected range will be displayed in a more detailed view as graph 401.

While the particular graph 401 illustrated in FIG. 4 shows a period of approximately 11 days and the particular sub-interface 403 illustrated in FIG. 4 shows a period of approximately 1 month, more or fewer days may be shown at one time. For example, if the application is running on a device such as a tablet, notebook, laptop, or desktop computer, which has a screen that is large compared to the screen of a smartphone, graph 401 and/or sub-interface 403 may display an extended time range in accordance with the larger screen. Thus, a user may be able to easily compare his or her environmental responses from season-to-season or understand how his or her environmental response cycles over the course of the year.

Furthermore, interface 400 may present the user with a notification ("information center") button 405, by which the user may receive or be apprised of pending messages, notifications, warnings, alerts, links to pertinent information within application 110 and/or elsewhere online (which information may, for example, be selected by the method specifically for a given user based upon the user's self-identified health conditions at the time the user established his or her account) and the like. Additionally and alternatively, message button 406 (e.g., a "Share" button) may provide an option by which the user may send (for example, via e-mail, text message, and/or other online messaging system) his or her "Aller-Rhythm™" display or symptom scores to another person; for example, the user's doctor, a social media account, or a family member of the user. Moreover, a "quick call" button 407 may be provided to connect a user to a medical professional or specialist with options to schedule an appointment, send a message, initiate a telephone or video call, and the like.

Figure 5A:
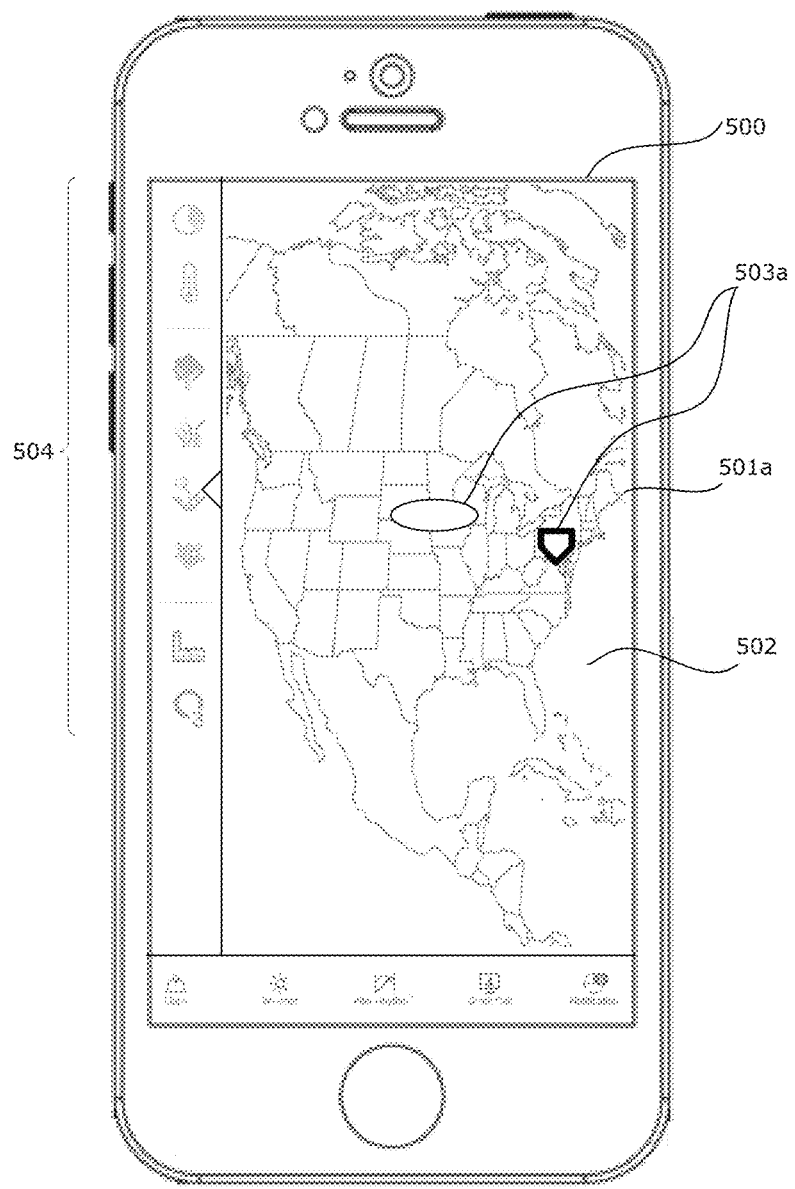
FIG. 5A-5B illustrate another exemplary interface generated by a symptom analysis application.
Figure 5B:
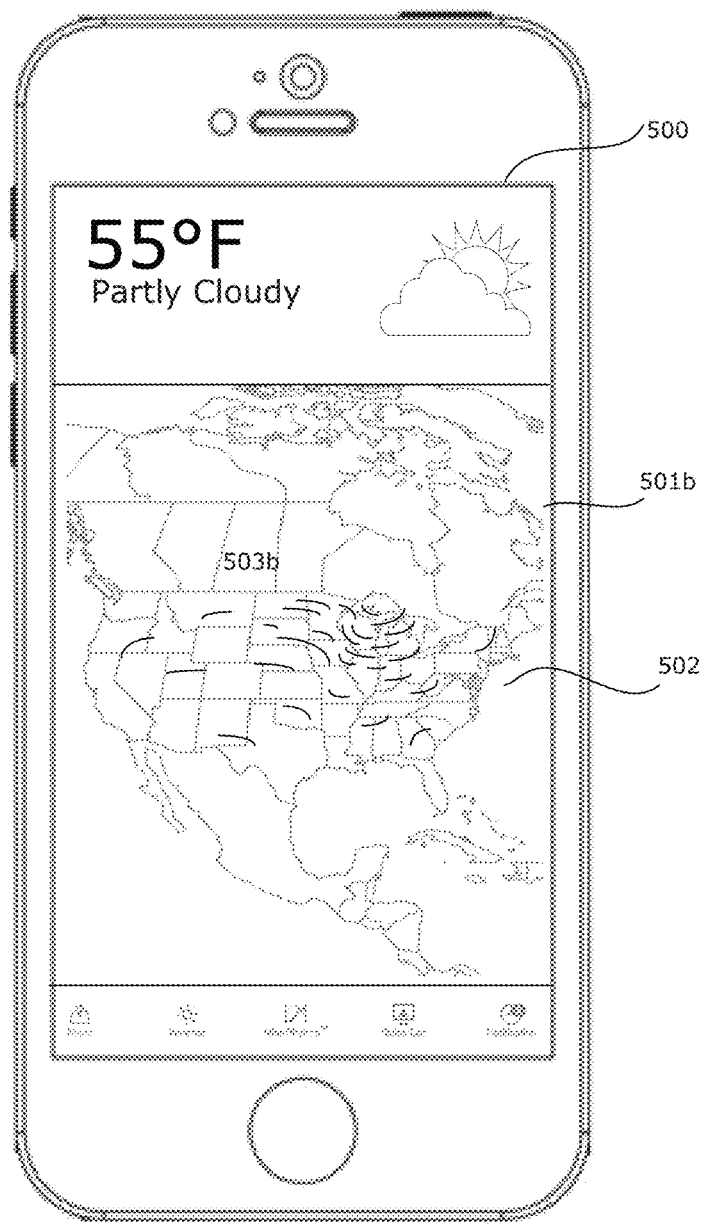

FIGS. 5A and 5B illustrate an exemplary map interface 500 generated by application 110 in a still mode and an animated mode, respectively. Interface 500 is a map overlay configured to apprise the user of current or historical environmental conditions that may affect his or her disease symptoms.

Application 110 is preferably configured to present data via interface 500 upon request by a user. Alternatively, application 110 may present interface 500 upon application start-up, when the user enters a particular geographic area, as a desktop widget for continuous viewing, or the like.

Interface 500 may present data in a graphical format, for example via map 501a or 501b. Map 501a presents a snapshot of environmental data for a particular time and/or a degree of risk of experiencing symptoms. For example, map 501a may correspond to environmental conditions in real time, one hour in the past, one day in the past, or the like. Additionally or alternatively, interface 500 is configured to present map 501b in animated form; for example, showing the recent distribution and/or change in environmental conditions and factors over a period of time immediately preceding the current time.

Map 501a preferably comprises a background map 502 and an overlay 503a. Background map 502 corresponds to a particular geographic region to be displayed. Preferably, interface 500 is configured to pan, scroll, rotate, and/or zoom map 501a (including background map 502) upon user input, in response to a hardware component contained in user device 120 (such as an accelerometer or the like), according to predefined display rules, etc. Preferably, background map 502 defaults to a display of a geographic region centered on the user's location. Alternatively or additionally, background map 502 may default to a home location set by the user.

Overlay 503a provides a visual representation of one or more environmental factors. In the particular interface 500 illustrated in FIG. 5A, overlay 503a is a heat map configured to convey information regarding a particular environmental factor according to color regions. Additionally or alternatively, overlay 503a may comprise a plurality of pins or flags configured to display information upon selection or activation by the user, for example, a user location.

In the particular interface 500 illustrated in FIG. 5B, overlay 503b may additionally or alternatively comprise an animated vector map created and developed by application 110, such as a wind map, that may also be used as a background for an overlay of other pollen, mold spore, weather, and environmental data. In this example, each particle in the animated system is assigned a color based upon a reference table obtained from a second set of environmental data (specifically, allergen data), as described in more detail below. The particles constituting animated overlay 503b may be colorized to reflect the relative risks of experiencing said medical conditions; for example, white for absent, green for low, yellow for moderate, orange for high, and red for very high. Additionally or alternatively, the particles constituting animated overlay 503b may be colorized to reflect severity or concentration of one or more of pollen, mold spore, weather, and environmental data. For example, each color may correspond to a particular range of pollen concentration.

In determining the relative risks of experiencing medical conditions, data particular to the user is used. For example, if a user has completed a questionnaire of the type described above with respect to FIG. 3A, the relative risk may be based at least in part on the user's calculated hypersensitivity score. Additionally, if the user has completed questionnaires of the type described above with respect to FIG. 3B with sufficient regularity, the relative risk may be based at least in part on the user's historical symptom data.

Moreover, the particles constituting animated overlay 503b may convey information by other attributes. For example, attributes such particle size (width and/or length), particle density, particle speed, or particle shape may differ depending on a physical quantity to be measured. In a preferred embodiment, a combination of attributes may be used to convey multiple attributes simultaneously. For example, animated overlay 503b may display particles with a density corresponding to a real-time measurement of the concentration of a particular allergen and with a color corresponding to the relative risks of experiencing medical conditions specific to the user.

Interface 500 may further include a plurality of map options 504. For example, interface 500 may present the user with a list of symptoms, allergens, data types, or the like, and the user may select the particular elements to be displayed via overlay 503a or 503b. Additionally, interface 500 may present the user with a plurality of options regarding length of historical data to display, speed and frame rate of animation, update interval, and the like.

While the particularly illustrated examples show overlay 503b as including a weather overlay, it should be understood that a similar overlay may be included in overlay 503a. Moreover, the weather overlay may include humidity data, dew point, wind speed, wind direction, pressure, forecast, and the like.

Figure 6:
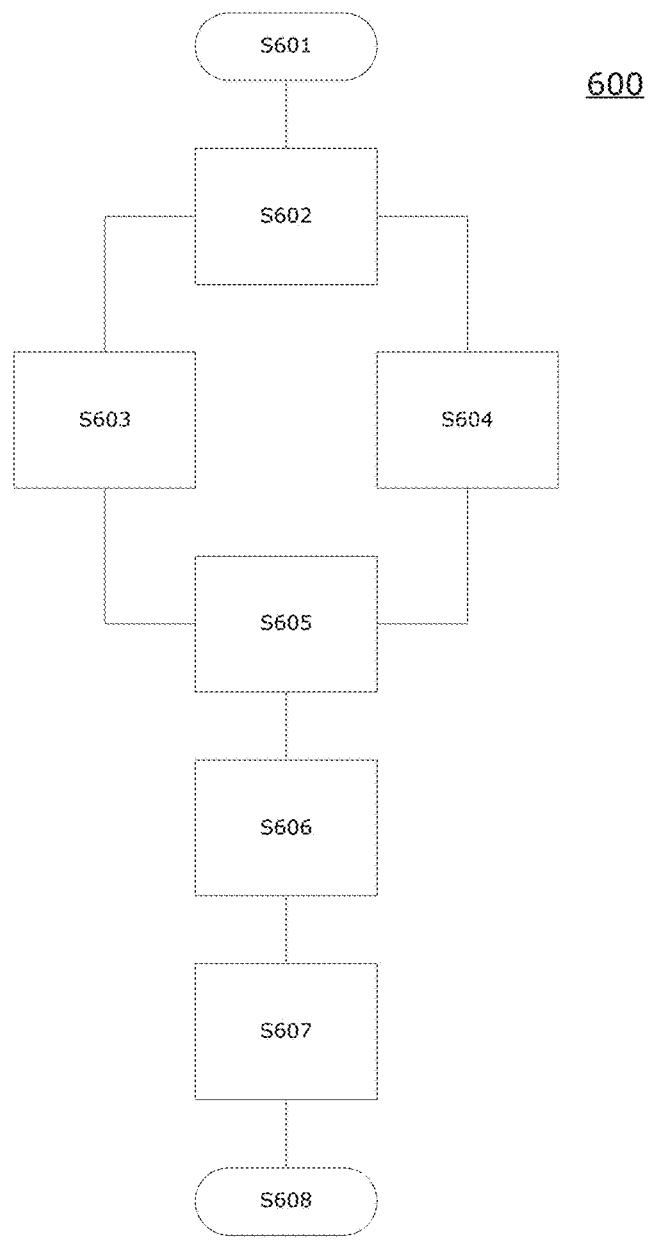
FIG. 6 illustrates an exemplary process flow of an implementation of a symptom analysis application in an analytic mode thereof.

FIG. 6 illustrates an exemplary process flow 600 of application 110 in an analytic mode thereof. Process 600 corresponds to a method for aggregating data, weighting the data, calculating a score, and presenting the results to a user. Individual steps S601-S608 are preferably performed by a processing unit, such as process 103 of one or more of devices 101, 120, 130.

The exemplary process 600 initiates at step S601; for example, based on a user input, a predetermined update interval, an administrator request, or the like. Upon initiation, process 600 proceeds to step S602 and initiates a data accumulation phase.

The data accumulation phase includes step S603 by which the process 600 aggregates user data and step S604 by which the process 600 aggregates environmental data. Steps S603 and S604 may be performed sequentially (that is, in series) or simultaneously (that is, in parallel). Additionally, process 600 may perform only one of steps S603 and S604 if, for example, only user data or only environmental data is required.

Step S603 may comprise administering a questionnaire to the user, such as a questionnaire of the type described above and administered via interface 300. Additionally or alternatively, step S603 may comprise aggregating historical user data, such as user data contained in a database 220 of the type described above.

Step S604 may comprise aggregating historical environmental data, such as environmental data contained in a database 220 of the type described above. Additionally or alternatively, step S604 may comprise querying a sensor network in real time to determine instantaneous environmental conditions.

After all necessary data has been aggregated, process 600 proceeds to step S605 and initiates a weighting phase. Step S605, as described above, may also be implemented using unique software programming involving a rule set, for example from memory 102 or database 220 of the type described above. The rule set may contain coefficients corresponding to the weight to be given to a particular data type. For example, the rule set may state that a user's responses to questionnaires are to be given the greatest weight, data regarding pollen count are to be given an intermediate weight, and data regarding temperature are to be given the least weight. Additionally, depending on the particular symptom or allergen being analyzed, a data type may be given zero weight. For example, where process 600 is analyzing asthma symptom scores, data regarding Peak Flow Meter data and fractional exhaled nitric oxide concentrations (FeNO) are given higher statistical weight, and graphed against environmental factors accordingly. Other environmental factors may be given no weight if, for example, the characteristic contained in the data type does not contribute to the particular symptom being analyzed.

After weights have been assigned to all required data types, process 600 proceeds to step S606 and initiates a calculation phase. Step S606 may comprise simple addition of weighted factors, collinear regression, historical user-specific data sets, and the like.

An exemplary calculation phase may comprise modeling a sub-score or the total score by the following expression (1):

$$S = \alpha_0 + \sum_i \alpha_i \cdot x_i \quad (1)$$

where S represents the score calculation, $a_0$ is a constant term, $x_i$ represents the value of a particular data type, and $a_i$ represents a coefficient representative of the weight assigned to the corresponding data type. The data types $x_i$ may be represented as continuous variables or dummy variables. Here, $a_0$ may correspond to the above-described hypersensitivity score, with or without a weight.

Continuous variables may include any data type capable of representation as a continuous range of values. For example, continuous variables may include, but are not limited to, one or more of temperature, humidity, pollen levels, mold spore levels, precipitation, ozone levels, particulate matter levels, and the like. For example, in step S606, score S may be increased by a value $\alpha_{mold}$ (or decreased if the value of $\alpha_{mold}$ is negative) for each unit increase in mold spore levels.

Dummy variables may include any data type capable of representation by either 1 or 0. For example, dummy variables may include, but are not limited to, whether wind speed is above a threshold level, whether a thunderstorm is expected within the next 12 hours, and the like. For example, in step S606, if a thunderstorm is expected within the next 12 hours, score S may be increased by a value $\alpha_{storm}$ (or decreased if the value of $\alpha_{storm}$ is negative).

Step S606 comprises analyzing and manipulating both incoming environmental data identified above (e.g., environmental data updated hourly or daily) and user's symptom scores collected as above and implemented using unique software programming, wherein pollen and mold spore information may be phase shifted by 24 hours, as such data commonly becomes available 24 hours after the measured quantity appears in the air; and visualization of animated relative risk maps (as illustrated in FIG. 5A-B) and graphic displays (as illustrated in FIG. 4) are created and modified by using the same unique software implementation to account for effects of precipitation (which decreases pollen levels concurrently), updrafts (which increases risks of exposures to mold spores); and hourly and daily water vapor images/data and soil moisture content (which affect exposures to airborne mold spores).

Preferably, step S606 comprises calculating a plurality of individual sub-scores corresponding to respective symptom scores and/or environmental-weather factor exposures. For example, process 600 may calculate a pollen sub-score, an asthma sub-score, a hay fever sub-score, and the like. Individual sub-scores may be stored as is and/or may be combined into a separate total score. If the total score or an individual sub-score exceeds a certain threshold, that particular symptom or environmental factor (i.e. allergen) may be flagged appropriately.

Step S606 may further comprise creating a data array based on the calculated data. For example, the data array may include a list of individual sub-scores along with their respective disease-specific symptom. Additionally or alternatively, the data array may include aggregate sub-scores and/or aggregate total scores corresponding to data compiled from a plurality of different users within a given geographic area. This data array may be compared with changes in specific environmental factors within the user's (or users') geographic area. In this manner, process 600 may collect and create data that reveals the probable cause or causes of a user's symptoms for one or more specific medical conditions.

Likewise, the data array may comprise a listing of current and historical environmental data collected and aggregated from a database (such as database 220 as described above). Rather than storing raw data, the data array may comprise manipulated particle system data derived from vector fields created by unique software implementing process 600. In this example, each particle in the system is assigned a color based upon a reference table obtained from a second set of environmental data (specifically, allergen data).

The reference table may provide a set of conditions for labeling each particle in the system. For example, the reference table may provide conditions for labeling allergen data as absent, low, moderate, or high. According to these labels, the system may be mapped in colors depending upon the airborne levels of each allergen or pollution factor; for example, white for absent, green for low, yellow for moderate, orange for high, and red for very high.

After calculation and score-assignment is complete, process 600 proceeds to step S607 and initiates a presentation phase. Step S607 may comprise presenting calculated data in one or a plurality of ways. For example, the calculated data may be presented via an output interface such as interface 400 described above. Additionally or alternatively, calculation results may be presented in raw (that is, textual as opposed to graphical) form. Still additionally, calculation results may be presented in an animated vector map form, for example depicting an individually-tailored risk of experiencing allergy and/or other disease-related symptoms based upon location such as interface 500 described above.

Step S607 preferably comprises the creation of an animated map, and/or a non-animated graphic that reveals the relative risk of the user experiencing symptoms of a medical condition previously selected by that user, which map or display visualization depends upon responses (symptom scores) of the user to questionnaires associated with that specific medical condition. The animated map or display may be colorized to reflect the relative risks of experiencing said medical conditions; for example, white for absent, green for low, yellow for moderate, orange for high, and red for very high.

Step S607 may utilize the data array created in step S606 to create a data visualization graph (i.e., an "AllerRhythm™" display of the type described above with reference to FIG. 4. Thereby, process 600 may present an easily-understandable visualization to the user that reveals the probable cause or causes of the user's symptoms for one or more specific medical conditions.

Step S607 may additionally or alternatively utilize the particle system data created in step S606 to create the animated map described above. In this example, each particle at each animation step is converted into polygons; for example, using a Voronoi tessellation. Each such polygon is then mapped to a color depending on the rule set described above. Where the animated map is a wind map, step S607 may comprise determining if a wind particle falls within the bounds of an allergen data polygon; if so, that particle inherits the allergen data polygon's color.

Preferably, the presentation phase presents individually unique data visualizations to the user, corresponding to the unique health status profile of the user. Additionally, step S607 may present background data to the user, such as articles, information, helpful hints, common treatments, and the like, corresponding to one or more health-related symptoms or associated allergens.

If any symptoms and/or allergens were flagged in step S606, calculation results corresponding to those symptoms and/or allergens may be highlighted or presented with priority. Furthermore, process 600 may query a database of medical professionals (for example, a database 220) and present the user with one or more of those professionals who specialize in the diagnosis and treatment of the flagged medical conditions. The list of professionals may be presented via a separate output interface, which interface may further include options to schedule an appointment, send a message, initiate a telephone or video call, and the like. The presented list of professionals may be based at least in part upon user symptom data such as data collected by interface 300 described above, user location data, and the like.

After the results have been presented (for example, after a predetermined period of time has passed or upon user input), process 600 proceeds to step S608 and terminates.

Figure 7:
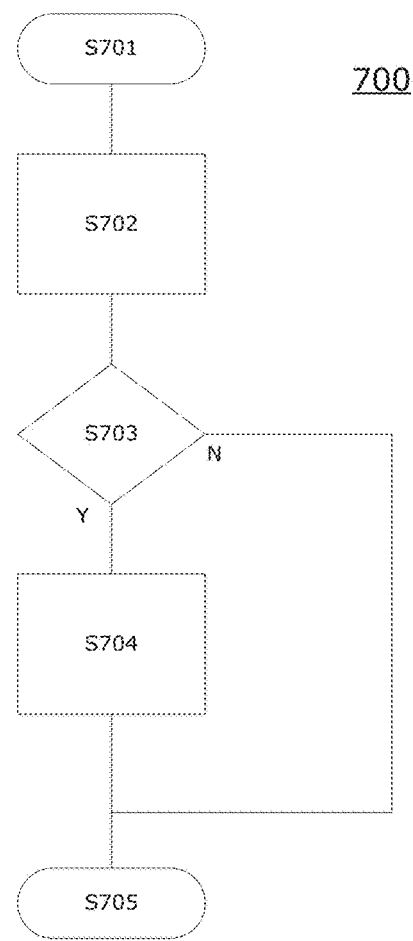
FIG. 7 illustrates an exemplary process flow of an implementation of a symptom analysis application in a monitoring mode thereof.

FIG. 7 illustrates an exemplary process flow 700 of application 110 in a monitoring mode thereof. Process 700 may correspond to a method for providing background monitoring of health characteristics without requiring continuous user attention. Individual steps S701-S705 are preferably performed by a processing unit, such as process 103 of one or more of devices 101, 120, 130.

The exemplary process 700 initiates at step S701; for example, based on a user input, application start-up, an administrator request, location data, or the like. Upon initiation, process 700 proceeds to step S702 and initiates a user information gathering phase.

The user information gathering phase may include acquiring location data; for example, from a Global Positioning System (GPS), via cellular tower triangulation, via data corresponding to local Wi-Fi hotspots, and the like. Step S702 may additionally or alternatively comprise receiving a notification message from a centralized server, or may comprise receiving a signal from user device 120 indicating that user device 120 has received a particular Radio Frequency Identification (RFID) or NFC signal.

Once the user information gathering phase has completed, process 700 proceeds to step S703 and determines whether any warnings and/or messages are required for delivery. If step S703 determines ("Y") that warnings and/or messages are required, process 700 proceeds to step S704 for sending the warnings and/or messages. If step S704 determines ("N") that no warnings and/or messages exist, process 700 may skip step S704. Afterward, process 700 may terminate at step S707. Alternatively, process 700 may return to start (that is, step S701) upon termination.

Where process 700 corresponds to an environmental alert warning system, step S703 may alert a user of environmental risks when process 700 determines that the user has entered a high-risk area. For example, where process 700 determines from the user information that the user has entered a high-smog area, process 700 may alert the user to that effect.

Alternatively, where process 700 corresponds to a marketing system, step S703 may alert the user of special marketing deals and/or discount coupons offered by nearby medical professionals, clinics, pharmacies, or the like. For example, where process 700 determines from the user information that the user is near a particular pharmacy (for example, a marketing partner pharmacy or a pharmacy which stocks a marketing partner product), process 700 may send the user an electronic coupon for the particular pharmacy and/or for a product to treat a particular symptom or allergen. Preferably, the electronic coupon or marketing offer is time sensitive and will disappear from user device 120 after the expiration of a predetermined time period; for example, several hours.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

The invention claimed is:

1. A method of presenting real-time health information, the method comprising steps of:
   (a) administering by a user interface associated with a mobile device, a virtual questionnaire to obtain information regarding the user's symptoms,
   (b) determining the location of the user using a location determination circuit associated with the mobile device;
   (c) obtaining environmental data from an internet-accessible database corresponding with the user's local environmental conditions at the time the questionnaire is administered;
   (d) automatically by a processor associated with the mobile device determining the health status of the user based on the user's response to the virtual questionnaire;
   (e) storing the health status of the user and corresponding environmental data in a data store associated with the mobile device;
   (f) developing a data structure from which the health status of the user is correlated with the user's local environmental conditions to identify causes of symptoms for the user;
   (g) repeating steps (a) through (e) a plurality of different times, and recorrelating health status with the user's local environmental conditions to refine and enhance the data structure;
   (h) determining at predetermined times the location of the user using the location determination circuit of the mobile device;
   (i) obtaining current or predicted environmental data from the internet-accessible database at the location determined in step (h) contemporaneously with step (h);
   (j) predicting future symptoms based upon the data structure and current or predicted local environmental conditions determined in step (i);

(k) determining whether to deliver a warning of environmental risks that are predicted to induce symptoms in the user; and (l) presenting by a display associated with the mobile device a visualization indicative of the future symptoms if it is determined that a warning is to be delivered wherein presenting the visualization includes:
generating a map image;
overlaying a plurality of animated particles over the map image; and
displaying the map image and the plurality of animated particles on the display.

2. The method according to claim 1, wherein a respective attribute of a corresponding animated particle is based on at least one of a relative risk of experiencing a symptom, a level of an external factor, and a past user health status.

3. The method according to claim 2, wherein the external factor is at least one of a mold spore count, a weather status, a pollen level, and an environmental data.

4. The method according to claim 2, wherein the attribute is at least one of a particle width, a particle length, a particle density, a particle speed, a particle color, and a particle shape.

5. The method according to claim 1, wherein presenting the visualization includes:
generating a graph, the graph indicating at least one of a series of past user-specific health statuses and a series of past external factors; and
displaying the graph on the display.

6. The method according to claim 1, wherein presenting the visualization includes:
generating a promotion for a product or service related to the instantaneous user health status; and
displaying a selectable icon corresponding to the promotion on the display.

7. The method according to claim 1, further comprising:
receiving by the user interface a request for contact with a professional; and
in response, establishing a connection between the mobile device and an external device associated with the professional.

8. The method according to claim 7, wherein the connection is one of a telephone connection, an instant messaging connection, and a video chat connection.

9. The method according to claim 1, further comprising:
periodically by the processor determining a predicted likelihood of a symptom occurrence; and
if the predicted likelihood of the symptom occurrence exceeds a predetermined threshold, generating a notification message and displaying the notification message on the display.

10. The method according to claim 1, wherein the virtual questionnaire is a virtual hypersensitivity test.

11. The method of claim 1, further comprising displaying the user's forecasted symptoms over a period of 4 to 7 days based on the data structure and predicted environmental conditions over the period.

12. An electronic system for presenting real-time health information, the system comprising:
a data store; and
a mobile device coupled to the data store and programmed to:
(a) administer by a user interface associated with a mobile device a virtual questionnaire to obtain information regarding the user's symptoms, (b) determining the location of the user using a location determination circuit associated with the mobile device;
(c) obtaining contemporaneous environmental data corresponding with the user's local environmental conditions;
(d) automatically by a processor associated with the mobile device determining the health status of the user based on the user's response to the virtual questionnaire;
(e) storing the symptom score and corresponding environmental data in a data store associated with the mobile device;
(f) developing a data structure from which the health status of the user is correlated with the user's local environmental conditions to identify causes of symptoms for the user;
(g) repeating steps (a) through (e) a plurality of different times, and recorrelating health status with the user's local environmental conditions to refine and enhance the data structure;
(h) determining at predetermined times the location of the user using the location determination circuit of the mobile device;
(i) obtaining current or predicted environmental data from the internet-accessible database at the location determined in step (h) contemporaneously with step (h);
(j) predicting future symptoms based upon the data structure and current or predicted environmental conditions; and
(k) presenting by a display associated with the mobile device a visualization indicative of the future symptoms, wherein presenting the visualization includes:
generating a map image;
overlaying a plurality of animated particles over the map image; and
displaying the map image and the plurality of animated particles on the display.

13. A method of presenting real-time health information for a user, the method comprising:
(a) administering by a user interface associated with a mobile device a virtual questionnaire to obtain information regarding the user's symptoms;
(b) acquiring time and using a location determination circuit to acquire location data for the user at a time contemporaneous with the administering of the virtual questionnaire;
(c) obtaining environmental data corresponding with the user's local environmental conditions from an internet-accessible database at a time contemporaneous with the administering of the virtual questionnaire;
(d) automatically by a processor associated with the mobile device determining the health status of the user based on the user's response to the virtual questionnaire;
(e) storing the health status of the user and corresponding environmental data in a data store associated with the mobile device;
(f) developing a data structure from which the health status of the user is correlated with the user's local environmental conditions to identify causes of symptoms for the user;
(g) repeating steps (a) through (e) a plurality of different times, and recorrelating health status with the user's local environmental conditions to refine and enhance the data structure;

(h) determining at predetermined times the location of the user using the location determination circuit of the mobile device;

(i) obtaining current or predicted environmental data from the internet-accessible database at the location determined in step (h) contemporaneously with step (h);

(j) predicting future symptoms based upon the data structure and current or predicted local environmental conditions; and (k) presenting by a display associated with the mobile device a visualization indicative of the future symptoms; wherein presenting the visualization includes:

generating a map image;

overlaying a plurality of animated particles over the map image; and displaying the map image and the plurality of animated particles on the display.

14. The method of claim 13, wherein the location data is acquired by the device from Global Positioning System.

15. The method of claim 13, wherein the location data is acquired by the device via cellular tower triangulation.

16. The method of claim 13, wherein the location data is acquired via data corresponding to local Wi-Fi hotspots.

17. The method of claim 13, wherein the environmental data is obtained by the device from a database.

18. The method of claim 17, wherein the data in the database is accessed via a wired or wireless network.

19. The method of claim 17, wherein the database is a weather database or public record database.

20. The method of claim 17, wherein the environmental data comprises at least one of temperature, humidity, wind speed, wind direction, pollen level, mold spore level, virus prevalence, precipitation, ozone level, particulate matter level, and barometric pressure.

* * * * *